United States Patent [19]

Farge et al.

[11] Patent Number: 4,556,657
[45] Date of Patent: Dec. 3, 1985

[54] 6-(1,8-NAPHTHYRIDIN-2-YL)-DITHIINO[1,4][2,3-C]-PYRROLES USEFUL AS TRANQUILLIZING AND ANTICONVULSANT AGENTS

[75] Inventors: Daniel Farge, Thiais; André Leger, Paris; Gerard Ponsinet, Sucy-en-Brie, all of France

[73] Assignee: Rhone-Poulenc Sante, Courbevoie, France

[21] Appl. No.: 487,132

[22] Filed: Apr. 21, 1983

[30] Foreign Application Priority Data

Apr. 22, 1982 [FR] France ................... 82 06943

[51] Int. Cl.$^4$ ................... C07D 401/14; C07D 417/14; A61K 31/495
[52] U.S. Cl. ................... 514/252; 544/362; 544/373; 544/377; 544/378; 546/113; 260/330.3
[58] Field of Search ............... 544/362, 373; 424/250

[56] References Cited

U.S. PATENT DOCUMENTS 3,948,917  4/1976  Jeanmart et al. ............ 544/373
4,021,554  5/1977  Cotrel et al. ................ 544/362
4,124,711  11/1978  Jeanmart et al. ............ 544/362
4,327,095  4/1982  Farge et al. ................ 544/362

OTHER PUBLICATIONS

Wolff, M. E., "Burger's Medicinal Chemistry", pp. 169-171, Part I, 4 ed., (1980), John Wiley & Sons, N.Y.

*Primary Examiner*—Donald G. Daus
*Assistant Examiner*—S. A. Gibson
*Attorney, Agent, or Firm*—Stevens, Davis, Miller & Mosher

[57] ABSTRACT

New compounds of the formula:

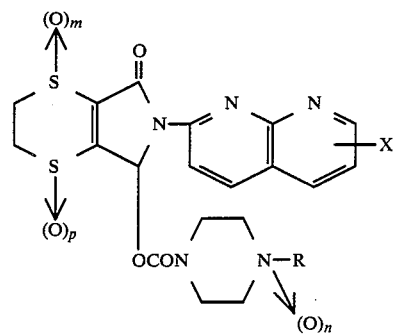

wherein X represents hydrogen, halogen, alkyl (1 to 4 C), alkoxy (1 to 4 C), cyano or nitro, R represents alkyl (1 to 4 C) optionally substituted by hydroxy, or alkenyl (2 to 4 C), and n represents 0 or 1, and one of the symbols m and p represents the figure 0 and the other represents the figure 1.

The new compounds are therapeutically useful, more particularly as tranquillizers and anticonvulsants.

7 Claims, No Drawings

6-(1,8-NAPHTHYRIDIN-2-YL)-DITHIINO[1,4][2,3-C]-PYRROLES USEFUL AS TRANQUILLIZING AND ANTICONVULSANT AGENTS

This invention relates to new therapeutically useful dithiino[1,4][2,3-c]pyrrole derivatives, to processes for their preparation and pharmaceutical compositions containing them.

The dithiino[1,4][2,3-c]pyrrole derivatives of the present invention are those of the general formula:

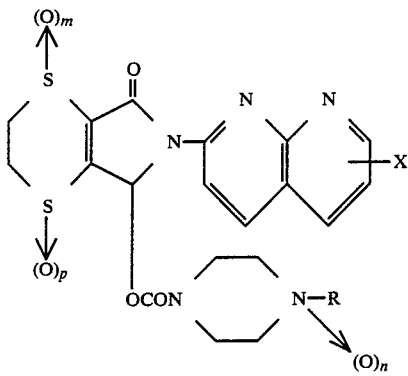

wherein X represents a hydrogen or halogen, preferably chlorine, atom or an alkyl radical containing 1 to 4 carbon atoms, an alkoxy radical containing 1 to 4 carbon atoms, a cyano radical or a nitro radical, R represents an alkyl radical containing 1 to 4 carbon atoms optionally substituted by a hydroxy radical, or an alkenyl radical containing 2 to 4 carbon atoms, n represents 0 or 1, and one of the symbols m and p represents the figure 0 and the other represents the figure 1, and acid addition salts thereof.

The aforementioned alkyl, alkoxy and alkenyl radicals may have straight- and branched-chains.

It is to be understood that the present invention relates to the compounds of general formula I in the cis and trans forms, both pure and as mixtures.

According to a feature of the invention, the compounds of general formula I, wherein the various symbols are as hereinbefore defined, are obtained by oxidising one of the sulphur atoms of a compound of the general formula:

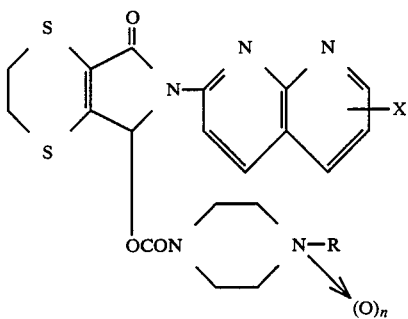

wherein X and R are as hereinbefore defined, and n represents 0 or 1 according to the definition of the symbol in general formula I to an —SO— radical, and then separating the products obtained.

The oxidation can be carried out using about one equivalent of an agent commonly used for converting a sulphide to a sulphoxide, the reaction being carried out in a suitable solvent. By way of example, it is possible to use hydrogen peroxide in acetone or acetic acid, an alkali metal periodate in an alcohol or acetonitrile, or a peroxycarboxylic acid, e.g. peracetic, perbenzoic, m-chloroperbenzoic, p-nitroperbenzoic or perphthalic acid, in an ether, e.g. dioxan, tetrahydrofuran or diethyl ether, a chlorinated solvent (e.g. methylene chloride or dichloroethane), acetic acid or a mixture of these solvents. The reaction is generally carried out at a temperature between $-10°$ and $+20°$ C.

It is particularly advantageous to carry out the reaction in a mixture of acetic acid and methylene chloride, in the presence of m-chloroperbenzoic acid, at a temperature between $-10°$ and $0°$ C.

According to another feature of the invention, the compounds of general formula I wherein n represents 1 and the other symbols are hereinbefore defined, are also obtained by oxidising a compound of the general formula:

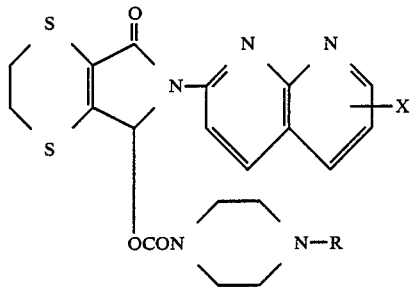

wherein R and X are as hereinbefore defined, to convert one of the sulphur atoms to a —SO— radical and the >N—R moiety to

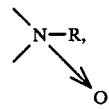

and then separating the products obtained.

In this case, the oxidation is carried out in the presence of at least two equivalents of an agent commonly used for oxidising both a sulphide and an amine in a suitable solvent. By way of example, it is possible to use hydrogen peroxide in acetone or acetic acid, or a peroxycarboxylic acid, e.g. peracetic, perbenzoic, m-chloroperbenzoic, p-nitroperbenzoic or perphthalic acid, in an ether, e.g. dioxan, tetrahydrofuran or diethyl ether, a chlorinated solvent, e.g. methylene chloride or dichloroethane, acetic acid or a mixture of these solvents. The reaction is generally carried out at a temperature between $-10°$ and $+20°$ C.

It is particularly advantageous to carry out the reaction in methylene chloride, in the presence of an excess of m-chloroperbenzoic acid, at a temperature between $-10°$ and $0°$ C.

The various oxidation products can be separated by any customary physical or chemical means known to those skilled in the art. It is particularly advantageous to carry out the separation by chromatography.

The starting materials of general formulae II and III can be prepared as described in U.S. Pat. No. 3,948,917 or British Pat. No. 1397060.

The new compounds of general formula I can be converted by known methods into acid addition salts. The acid addition salts can be obtained by reacting the dithiino[1,4][2,3-c]pyrrole derivatives with acids in appropriate solvents. As organic solvents there can be used alcohols, ethers, ketones or chlorinated solvents. The salt which is formed is precipitated, if necessary after concentration of the solution, and is isolated by filtration or decantation.

Of particular value are the compounds of general formula I wherein X represents a halogen atom, R represents an alkyl radical containing 1 to 4 carbon atoms in a straight- or branched-chain, and n, and m and p are as hereinbefore defined.

The following are of particularly outstanding interest:

6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 4-oxide, trans form;

6-(7-chloro-1,8-naphthyridin-2-yl)-5-[(4-methylpiperazin-1-yl)carbonyloxy]-7-oxo-2,3,6,7-tetrahydro-5H-dithiino-[1,4][2,3-c]pyrrole 4-oxide, cis form;

6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 1-oxide, mixture of cis+- trans forms;

4-{[6-(7-chloro-1,8-naphthyridin-2-yl)-7-oxo-2,3,6,7-tetrahydro-5H-dithiino[1,4][2,3-c]pyrrol-5-yl 1-oxide]-oxycarbonyl}-1-methylpiperazine 1-oxide, mixture of cis+trans forms, and non-toxic pharmaceutically acceptable acid addition salts thereof.

The dithiino[1,4][2,3-c]pyrrole compounds of general formulae II and III have a tranquillising, anticonvulsant and hypnogenic action. It has now been found that the new compounds according to the present invention, i.e. the corresponding monosulphoxides, possess a tranquillising and anticonvulsant activity similar to that of the compounds of general formulae II and III, but have weaker "hypnogenic" properties which render them more suitable for the treatment of certain maladies, for example anxiety states and epilepsy.

The tranquillising activity of the compounds according to the present invention can be demonstrated on animals, viz mice, at doses of between 1 and 10 mg/kg, administered orally, in the pentetrazole-induced convulsions test, in accordance with a technique similar to that of EVERETT and RICHARDS, J. Pharmacol, Exp. Ther. 81, 402 (1944).

Administered orally to mice, in the test for potentiation of a small dose of chlorpromazine, measured in the Righting Reflex test, according to ZBINDEN and RANDALL, Advances in Pharmacology, 5, 213–291 (1967), a test making it possible to predict the "hypnogenic" effects of a product, the products according to the invention were only shown to be active at doses of more than 30 mg/kg.

Furthermore, the products according to the present invention have a low toxicity. In mice, the acute toxicity expressed by its $LD_{50}$, is generally between 300 and 900 mg/kg or even more than 900 mg/kg.

The following non-limitative Examples illustrate the preparation of compounds of the present invention.

EXAMPLE 1

A solution of 80% pure 3-chloroperbenzoic acid (24 g) in methylene chloride (500 cc) is added, with stirring, to a solution of 6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole (47.3 g) in methylene chloride (750 cc) and acetic acid (150 cc), cooled to −10° C. The addition is carried out dropwise in the course of 15 minutes so as to keep the temperature at between −10° and −5° C. After stirring for a further 30 minutes, diethyl ether (3 liters) is added and the mixture is then filtered in order to separate a solid product A and the mother liquors B.

The solid A is washed with diethyl ether (200 cc) and dried under reduced pressure (0.2 mm Hg; 0.027 kPa) at 20° C. The product obtained is chromatographed on silica gel (0.04–0.06 mm; 300 g) contained in a column of diameter 6 cm. Elution is carried out with a mixture of chloroform (4500 cc) and methanol (300 cc) and then with a mixture of chloroform (1500 cc) and methanol (150 cc), 100 cc fractions being collected. Fractions 9 to 15 are combined and the solvent is evaporated off under reduced pressure (20 mm Hg; 2.7 kPa) at 40° C. The residue is dissolved in a mixture of methylene chloride (140 cc) and methanol (20 cc), decolorising charcoal is added and the mixture is filtered. Diethyl ether (200 cc) is added to the filtrate. The crystals which form are filtered off and dried under reduced pressure (0.2 mm Hg; 0.027 kPa) at 40° C. This gives a mixture of the cis and trans diastereoisomers of 6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 1-oxide (9.3 g) melting with decomposition at about 255° C.

Fractions 21 to 39 from the above chromatography are combined and evaporated under reduced pressure (20 mm Hg; 2.7 kPa) at 40° C. The residue is chromatographed on silica gel (0.04–0.06 mm) (100 g) contained in a column of diameter 4 cm. Elution is carried out with a mixture of chloroform (1000 cc) and methanol (800 cc), 50 cc fractions being collected. Fractions 12 and 13 are combined, the solvent is evaporated off under reduced pressure (20 mm Hg; 2.7 kPa) at 40° C., and the residue is dried under reduced pressure (0.2 mm Hg; 0.027 kPa) at 60° C. This gives cis-6-(7-chloro-1,8-naphthyridin-2-yl)-5-[(4-methylpiperazin-1-yl)-carbonyloxy]-7-oxo-2,3,6,7-tetrahydro-5H-dithiino[1,4]-[2,3-c]pyrrole 4-oxide (0.94 g) melting with decomposition at about 250° C.

The mother liquors B are concentrated to dryness under reduced pressure (20 mm Hg; 2.7 kPa) at 50° C. The residue is triturated in diethyl ether (300 cc). The suspension obtained is filtered. The solid filtered off is dissolved in boiling ethanol (80 cc). The solution is cooled and the crystals obtained are filtered off. The mother liquors are concentrated to dryness under reduced pressure (20 mm Hg; 2.7 kPa) at 40° C., and the residue is chromatographed on silica gel (0.04–0.06 mm; 300 g) contained in a column of diameter 6 cm. Elution is carried out with chloroform (12 liters) containing methanol (from 5 to 20% by volume), 100 cc fractions being collected. The fractions obtained by elution with the 80/20 (by volume) chloroform/methanol mixture are combined and concentrated to dryness under reduced pressure (20 mm Hg; 2.7 kPa) at 40° C., and the residue is dried under reduced pressure (0.2 mm Hg; 0.027 kPa) at 60° C. This gives trans-6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 4-oxide (1.1 g) melting with decomposition at about 235° C.

EXAPLE 2

A solution of 80% pure 3-chloroperbenzoic acid (16.69 g) in methylene chloride (150 cc) is added to a solution of 6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole (19.12 g) in methylene chloride (250 cc), cooled to −10° C. The addition is carried out dropwise in the course of 30 minutes so as to keep the temperature at between −10° C. and −5° C. Stirring is continued for a further two hours at this temperature and the mixture is then filtered, the filtrate being collected in diethyl ether (800 cc). The precipitate obtained is filtered off, washed with diethyl ether and dried in air. This product is taken up in boiling ethanol (700 cc) containing decolorising charcoal (2 g), the mixture is filtered hot and the filtrate is cooled to 0° C. The crystals formed are filtered off, washed with ethanol (50 cc) and dried under reduced pressure (0.2 mm Hg; 0.027 kPa) at 60° C. This gives a mixture of the cis and trans diastereoisomers of 4-{[6-(7-chloro-1,8-naphthyridin-2-yl)-7-oxo-2,3,6,7-tetrahydro-5H-dithiino[1,4][2,3-c]-pyrrol-5-yl 1-oxide]oxycarbonyl}-1-methylpiperazine 1-oxide 3-chlorobenzoate (15 g), melting with decomposition at about 190° C.

For therapeutic purposes, the dithiino[1,4][2,3-c]pyrrole derivatives of general formula I are employed as such or in the form of pharmaceutically acceptable acid addition salts, i.e. salts which are non-toxic at the use doses. Examples of pharmaceutically acceptable acid addition salts are those with inorganic acids, such as the hydrochlorides, sulphates, nitrates and phosphates, or organic acids, such as the acetates, propionates, succinates, benzoates, fumarates, maleates, tartrates, theophyllinacetates, salicylates, phenolphthalinates and methylene-bis-β-oxynaphthoates, or substitution derivatives of such acids.

The present invention includes within its scope pharmaceutical compositions comprising at least one of the compounds of general formula I, or a pharmaceutically acceptable acid addition salt thereof, in association with any other pharmaceutically compatible product, which can be inert or physiologically active. The compositions can be administered orally, parenterally or rectally.

Tablets, pills, powders, in particular in gelatin capsules or in cachets, or granules can be used as solid compositions for oral administration. In these compositions, the active product according to the invention is mixed with one or more inert diluents such as starch, cellulose, sucrose, lactose or silica. These compositions can also comprise substances other than diluents, e.g. one or more lubricants such as magnesium stearate or talc, a dyestuff, a coating as in coated tablets or a varnish.

Liquid compositions for oral administration include pharmaceutically acceptable solutions, suspensions, emulsions, syrups and elixirs containing inert diluents commonly used in the art, such as water, ethanol, glycerol, vegetable oils or paraffin oil. These compositions can also comprise substances other than diluents, e.g. wetting, sweetening, thickening, flavouring or stabilising products.

Pharmaceutical compositions for parenteral administration include sterile aqueous or non-aqueous solutions, suspension or emulsions. Examples of suitable non-aqueous solvents or vehicles are propylene glycol, a polyethylene glycol, vegetable oils, in particular olive oil, and injectable organic esters such as ethyl oleate.

These compositions can also contain adjuvants, in particular wetting agents, agents for imparting isotonicity, emulsifiers, dispersants and stabilisers. Sterilisation can be carried out in several ways, e.g. by aseptic filtration, by incorporating sterilising agents into the composition, by irradiation or by heating. The compositions can also be prepared in the form of sterile solid compositions which can be dissolved in an injectable sterile medium at the time of use.

The compositions for rectal administration are suppositories or rectal capsules, which contain, in addition to the active product, excipients such as cacao butter, semi-synthetic glycerides or polyethylene glycols.

In human therapy, the compounds of the present invention are particularly useful in the treatment of certain diseases manifesting themselves as anxiety states or epileptiform states. The doses depend on the desired effect and the duration of the treatment; adult doses are generally between 0.2 and 50 mg per day, administered orally in one or more dosage units.

In general, the physician will determine the dosage which he considers to be most appropriate taking into account the age, the weight and all the other factors intrinsic to the patient being treated.

The following Example illustrates pharmaceutical compositions according to the invention.

EXAMPLE 3

Tablets containing a 10 mg dose of active product and having the following composition are prepared by the usual technique:

| | |
|---|---|
| mixture of cis and trans diastereoisomers of 6-(7-chloro-1,8-naphthyridin-2-yl)-5-[(4-methylpiperazin-1-yl)carbonyloxy]-7-oxo-2,3,6,7-tetrahydro-5H—dithiino[1,4]-[2,3-c]pyrrole 1-oxide | 10 mg |
| starch | 60 mg |
| lactose | 50 mg |
| magnesium stearate | 2 mg |

We claim:
1. A pure [1,4][2,3-c]pyrrole of the formula:

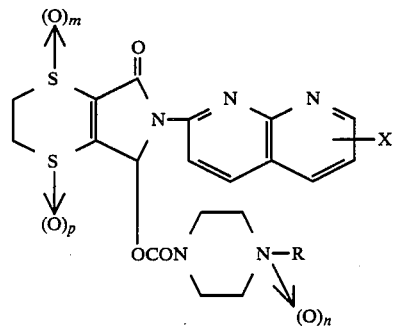

wherein X represents a hydrogen or halogen atom or an alkyl radical containing 1 to 4 carbon atoms, an alkoxy radical containing 1 to 4 carbon atoms, a cyano radical or a nitro radical, R represents an alkyl radical containing 1 to 4 carbon atoms optionally substituted by a hydroxy radical, or an alkenyl radical containing 2 to 4 carbon atoms, n represents 0 or 1, and one of the symbols m and p represents the figure 0 and the other represents the figure 1, and non-toxic pharmaceutically acceptable acid addition salts thereof.

2. A pure [1,4][2,3-c]pyrrole according to claim 1 wherein X represents a halogen atom, R represents an alkyl radical containing 1 to 4 carbon atoms, and n, and m and p are as defined in claim 1.

3. A pure [1,4][2,3-c] according to claim 1 which is 6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 4-oxide and its non-toxic pharmaceutically acceptable acid addition salts.

4. A pure [1,4][2,3-c]pyrrole according to claim 1 which is 6-(7-chloro-1,8-naphthyridin-2-yl)-5-[(4-methylpiperazin-1-yl)carbonyloxy]-7-oxo-2,3,6,7-tetrahydro-5H-dithiino[1,4][2,3-c]pyrrole 1-oxide and its non-toxic pharmaceutically acceptable acid addition salts.

5. A pure [1,4][2,3-c] according to claim 1 which is 4-{6-(7-chloro-1,8-naphthyridin-2-yl)-7-oxo-2,3,6,7-tetrahydro-5H-dithiino[1,4][2,3-c]pyrrole-5-yl 1-oxide]oxycarbonyl{-1-methylpiperazine 1-oxide and its non-toxic pharmaceutically acceptable acid addition salts.

6. A pharmaceutical composition useful as a tranquilizer and anticonvulsant which comprises a dithiino[1,4][2,3-c]pyrrole as claimed in claim 1, 2, 3, 4 or 5, or a non-toxic pharmaceutically acceptable acid addition salt thereof, in association with a pharmaceutical carrier.

7. A method for the treatment of a patient suffering from an anxiety state or an epileptiform state which comprises administering to the patient a tranquilliser or anticonvulsant of the formula depicted in claim 1, wherein X, R, n, m and p are as defined in claim 1, or a non-toxic pharmaceutically acceptable acid addition salt thereof, sufficient to ameliorate the condition of the patient.

* * * * *